United States Patent
Rezach et al.

(10) Patent No.: US 11,291,477 B1
(45) Date of Patent: Apr. 5, 2022

(54) DORSAL ADJUSTING IMPLANT AND METHODS OF USE

(71) Applicant: Warsaw Orthopedic, Inc., Warsaw, IN (US)

(72) Inventors: William A. Rezach, Covington, TN (US); Jerald L. Redmond, Germantown, TN (US); Jeffrey W. Beale, Germantown, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 0 days.

(21) Appl. No.: 17/307,674

(22) Filed: May 4, 2021

(51) Int. Cl.
*A61B 17/70* (2006.01)
*A61B 17/88* (2006.01)

(52) U.S. Cl.
CPC ...... *A61B 17/7008* (2013.01); *A61B 17/7032* (2013.01)

(58) Field of Classification Search
CPC .................. A61B 17/7008; A61B 17/7032
USPC .................. 606/264–275, 315–317
See application file for complete search history.

(56) References Cited

U.S. PATENT DOCUMENTS

| | | | |
|---|---|---|---|
| 3,604,487 A | 9/1971 | Gilbert | |
| 3,844,291 A | 10/1974 | Moen | |
| 4,411,259 A | 10/1983 | Drummond | |
| 5,020,519 A | 6/1991 | Hayes et al. | |
| 5,113,685 A | 5/1992 | Asher et al. | |
| 5,207,678 A | 5/1993 | Harms et al. | |
| 5,314,431 A | 5/1994 | Graziano | |
| 5,330,472 A | 7/1994 | Metz-Stavenhagen | |
| 5,364,397 A | 11/1994 | Hayes et al. | |
| 5,389,099 A | 2/1995 | Hartmeister et al. | |
| 5,443,467 A * | 8/1995 | Biedermann | A61B 17/7037 606/65 |
| 5,449,361 A | 9/1995 | Preissman | |
| 5,458,608 A | 10/1995 | Wortrich | |
| 5,466,243 A | 11/1995 | Schmieding et al. | |
| 5,575,792 A | 11/1996 | Errico et al. | |
| 5,609,593 A | 3/1997 | Errico et al. | |

(Continued)

FOREIGN PATENT DOCUMENTS

| | | |
|---|---|---|
| DE | 4238339 A1 | 5/1994 |
| DE | 4238339 C2 | 10/1994 |

(Continued)

*Primary Examiner* — Ellen C Hammond
*Assistant Examiner* — David C Comstock
(74) *Attorney, Agent, or Firm* — Fox Rothschild LLP

(57) ABSTRACT

An implant system is disclosed. The system may include an implant receiver having a base and a first arm and a second arm extending from the base in a longitudinal direction towards an open end. The first arm and second arm may define a receiving cavity therebetween. The first and second arm may each include an outside thread pattern for rotatably supporting a nut movable in the longitudinal direction and an inside thread pattern for rotatably supporting a set screw movable in the longitudinal direction. A rod may be selectively positioned within the receiving cavity at an intermediate elevation between the base and the open end and the rod may be supported by the nut. The set screw may be tightened against the rod thereby locking the rod and nut at the intermediate elevation. In some embodiments, the first and second arms may include a plurality of breakoff locations.

21 Claims, 15 Drawing Sheets

(56) References Cited

U.S. PATENT DOCUMENTS

| | | | |
|---|---|---|---|
| 5,609,654 A | 3/1997 | Le et al. |
| 5,616,143 A | 4/1997 | Schlapfer et al. |
| 5,630,817 A | 5/1997 | Rokegem et al. |
| 5,643,263 A | 7/1997 | Simonson |
| 5,683,391 A | 11/1997 | Boyd |
| 5,720,751 A | 2/1998 | Jackson |
| 5,782,830 A | 7/1998 | Farris |
| 5,797,911 A | 8/1998 | Sherman et al. |
| 5,885,285 A | 3/1999 | Simonson |
| 5,899,901 A | 5/1999 | Middleton |
| 5,910,141 A | 6/1999 | Morrison et al. |
| 5,944,720 A | 8/1999 | Lipton |
| 5,947,967 A | 9/1999 | Barker |
| 5,964,760 A * | 10/1999 | Richelsoph ........ A61B 17/7037 606/278 |
| 6,036,692 A | 3/2000 | Burel et al. |
| 6,042,582 A | 3/2000 | Ray |
| 6,063,088 A | 5/2000 | Winslow |
| 6,074,391 A | 6/2000 | Metz-Stavenhagen et al. |
| 6,280,442 B1 | 8/2001 | Barker et al. |
| 6,415,693 B1 | 7/2002 | Simon et al. |
| 6,440,133 B1 | 8/2002 | Beale et al. |
| 6,497,166 B1 | 12/2002 | Fleckenstein |
| 6,520,962 B1 | 2/2003 | Taylor et al. |
| 6,562,038 B1 | 5/2003 | Morrison |
| 6,572,618 B1 | 6/2003 | Morrison |
| 6,579,292 B2 | 6/2003 | Taylor |
| 6,648,887 B2 | 11/2003 | Ashman |
| 6,685,705 B1 | 2/2004 | Taylor |
| 6,755,830 B2 | 6/2004 | Minfelde et al. |
| 6,857,343 B1 | 2/2005 | Easterbrooks et al. |
| 6,872,209 B2 | 3/2005 | Morrison |
| 6,945,933 B2 | 9/2005 | Branch et al. |
| 7,066,939 B2 | 6/2006 | Taylor |
| 7,226,453 B2 | 6/2007 | Chao et al. |
| 7,572,264 B2 | 8/2009 | Null et al. |
| 7,771,459 B2 | 8/2010 | von Oepen |
| 7,846,167 B2 | 12/2010 | Garcia et al. |
| 7,947,047 B2 | 5/2011 | Arnal |
| 7,976,463 B2 | 7/2011 | Dewey et al. |
| 7,988,699 B2 | 8/2011 | Martz et al. |
| 8,048,124 B2 | 11/2011 | Chin et al. |
| 8,100,916 B2 | 1/2012 | Kumar et al. |
| 8,221,431 B2 | 7/2012 | Chenaux |
| 8,231,635 B2 | 7/2012 | Sharifi-Mehr et al. |
| 8,262,670 B2 | 9/2012 | Laubert et al. |
| 8,343,165 B2 | 1/2013 | Berrevoets |
| 8,394,108 B2 | 3/2013 | McLean et al. |
| 8,459,155 B2 | 6/2013 | Canizares, Jr. et al. |
| 8,460,307 B2 | 6/2013 | Saidha et al. |
| 8,475,466 B2 | 7/2013 | Chenaux |
| 8,540,756 B2 | 9/2013 | Olsen et al. |
| 8,585,741 B2 | 11/2013 | Gabelberger et al. |
| 8,747,411 B2 | 6/2014 | Mitchell |
| 8,757,035 B2 | 6/2014 | Kerboul et al. |
| 8,763,499 B2 | 7/2014 | Dahners |
| 8,784,431 B1 | 7/2014 | Harder et al. |
| 8,806,973 B2 | 8/2014 | Ross et al. |
| 8,845,652 B2 | 9/2014 | Heinz |
| 8,882,775 B2 | 11/2014 | LaPosta et al. |
| 8,900,248 B2 | 12/2014 | Biyani |
| 8,900,280 B2 | 12/2014 | Paroth et al. |
| 8,932,303 B2 | 1/2015 | Bouliane |
| 8,945,193 B2 | 2/2015 | Kirschman |
| 8,951,264 B2 | 2/2015 | Saidha et al. |
| 8,968,276 B2 | 3/2015 | Zemlok et al. |
| 8,992,575 B1 | 3/2015 | Di Lauro et al. |
| 8,992,587 B2 | 3/2015 | Kirschman |
| 8,998,921 B2 | 4/2015 | Sharifi-Mehr et al. |
| 9,017,333 B2 | 4/2015 | Beale et al. |
| 9,055,943 B2 | 6/2015 | Zemlok et al. |
| 9,089,371 B1 | 7/2015 | Faulhaber |
| 9,113,976 B2 | 8/2015 | Yevmenenko et al. |
| 9,138,279 B2 | 9/2015 | Laposta et al. |
| 9,149,307 B2 | 10/2015 | Sandstrom et al. |
| 9,216,044 B2 | 12/2015 | Nuckley et al. |
| 9,265,540 B2 | 2/2016 | Kirschman |
| 9,295,500 B2 | 3/2016 | Marigowda |
| 9,314,274 B2 | 4/2016 | Amstutz et al. |
| 9,387,025 B2 | 7/2016 | Santangelo et al. |
| 9,402,663 B2 | 8/2016 | Peterson et al. |
| 9,446,507 B2 | 9/2016 | Nino et al. |
| 9,526,553 B2 | 12/2016 | Bess et al. |
| 9,572,605 B2 | 2/2017 | Shipp |
| 9,597,135 B1 | 3/2017 | Miller et al. |
| 9,642,654 B2 | 5/2017 | Reimels et al. |
| 9,649,139 B2 | 5/2017 | Sharifi-Mehr et al. |
| 9,687,285 B2 | 6/2017 | Robinson |
| 9,724,149 B2 | 8/2017 | Trieu et al. |
| 9,808,354 B2 | 11/2017 | Willis et al. |
| 9,820,740 B2 | 11/2017 | Zemlok et al. |
| 9,855,087 B2 | 1/2018 | Divincenzo et al. |
| 9,949,731 B2 | 4/2018 | Erramilli et al. |
| 9,956,003 B2 | 5/2018 | Prevost |
| 9,968,384 B2 | 5/2018 | Fischer et al. |
| 9,987,066 B2 | 6/2018 | Stad et al. |
| 10,045,787 B2 | 8/2018 | Krebs et al. |
| 10,076,374 B2 | 9/2018 | Diduch et al. |
| 10,105,165 B2 | 10/2018 | Biedermann et al. |
| 10,117,684 B2 | 11/2018 | Saidha et al. |
| 10,160,105 B2 | 12/2018 | Nino et al. |
| 10,219,854 B2 | 3/2019 | Nino et al. |
| 10,274,021 B2 | 4/2019 | Victor et al. |
| 10,285,740 B2 | 5/2019 | May et al. |
| 10,349,986 B2 | 7/2019 | Wall et al. |
| 10,363,073 B2 | 7/2019 | Raina et al. |
| 10,390,967 B2 | 8/2019 | Livorsi et al. |
| 10,426,535 B2 | 10/2019 | Zander et al. |
| 10,433,883 B2 | 10/2019 | DiVincenzo et al. |
| 10,433,982 B2 | 10/2019 | Willis et al. |
| 10,448,978 B2 | 10/2019 | Wall et al. |
| 10,463,404 B2 | 11/2019 | Wall et al. |
| 10,470,805 B2 | 11/2019 | Biedermann et al. |
| 10,478,235 B2 | 11/2019 | Beale et al. |
| 10,568,668 B2 | 2/2020 | Biedermann et al. |
| 10,568,677 B2 | 2/2020 | DiVincenzo et al. |
| 10,582,925 B2 | 3/2020 | Marks et al. |
| 10,603,078 B2 | 3/2020 | Simpson et al. |
| 10,639,080 B2 | 5/2020 | Sharifi-Mehr et al. |
| 10,646,261 B2 | 5/2020 | Folger et al. |
| 10,653,457 B2 | 5/2020 | Erramilli et al. |
| 10,660,687 B2 | 5/2020 | Goodwin, Jr. et al. |
| 10,682,167 B2 | 6/2020 | Sandstrom et al. |
| 10,702,315 B2 | 7/2020 | Lindner |
| 10,702,316 B2 | 7/2020 | Heuer |
| 10,709,488 B2 | 7/2020 | Diduch et al. |
| 10,729,419 B2 | 8/2020 | Diduch et al. |
| 10,751,092 B2 | 8/2020 | Biedermann et al. |
| 10,765,466 B2 | 9/2020 | Stad et al. |
| 10,779,872 B2 | 9/2020 | Smith et al. |
| 10,869,751 B2 | 12/2020 | Diduch et al. |
| 10,874,448 B2 | 12/2020 | Rees et al. |
| 2002/0166421 A1 | 11/2002 | Bowerman |
| 2002/0169453 A1 | 11/2002 | Berger |
| 2003/0130659 A1* | 7/2003 | Haider ............... A61B 17/7032 606/302 |
| 2005/0159750 A1 | 7/2005 | Doherty |
| 2005/0273101 A1 | 12/2005 | Schumacher |
| 2006/0041261 A1 | 2/2006 | Osypka |
| 2006/0058794 A1* | 3/2006 | Jackson ............. A61B 17/7001 606/272 |
| 2006/0241593 A1 | 10/2006 | Sherman et al. |
| 2006/0241600 A1 | 10/2006 | Ensign et al. |
| 2007/0010816 A1 | 1/2007 | Wilkinson et al. |
| 2007/0122764 A1 | 5/2007 | Balfour et al. |
| 2008/0015596 A1 | 1/2008 | Whipple |
| 2008/0041196 A1 | 2/2008 | Companioni et al. |
| 2008/0071274 A1 | 3/2008 | Ensign |
| 2008/0147126 A1 | 6/2008 | Tipirneni et al. |
| 2008/0147128 A1 | 6/2008 | Fritzinger |
| 2008/0200918 A1 | 8/2008 | Spitler et al. |
| 2008/0215099 A1 | 9/2008 | Balfour et al. |
| 2008/0269768 A1 | 10/2008 | Schwager et al. |
| 2009/0005787 A1 | 1/2009 | Crall et al. |

(56) References Cited

U.S. PATENT DOCUMENTS

| | | |
|---|---|---|
| 2009/0264895 A1 | 10/2009 | Gasperut et al. |
| 2010/0249798 A1 | 9/2010 | Sournac et al. |
| 2010/0249846 A1 | 9/2010 | Simonson |
| 2011/0077693 A1 | 3/2011 | Yu |
| 2011/0125196 A1* | 5/2011 | Quevedo .............. A61B 90/50 606/308 |
| 2011/0137320 A1 | 6/2011 | von Oepen |
| 2011/0160775 A1 | 6/2011 | Carls et al. |
| 2011/0270321 A1 | 11/2011 | Prevost et al. |
| 2011/0270322 A1 | 11/2011 | Olsen et al. |
| 2011/0282398 A1 | 11/2011 | Overes et al. |
| 2011/0301650 A1 | 12/2011 | Johnson et al. |
| 2012/0123481 A1 | 5/2012 | Lin |
| 2012/0203288 A1 | 8/2012 | Lange et al. |
| 2012/0215263 A1 | 8/2012 | Lee |
| 2012/0239095 A1 | 9/2012 | Barrall |
| 2012/0253398 A1 | 10/2012 | Metcalf et al. |
| 2013/0072984 A1 | 3/2013 | Robinson |
| 2013/0072986 A1 | 3/2013 | Robinson |
| 2013/0261671 A1 | 10/2013 | Horvath |
| 2014/0018816 A1 | 1/2014 | Fenn et al. |
| 2014/0066945 A1 | 3/2014 | Humphreys et al. |
| 2014/0142639 A1 | 5/2014 | Vennard et al. |
| 2014/0172027 A1 | 6/2014 | Biedermann et al. |
| 2014/0257411 A1 | 9/2014 | Rezach |
| 2014/0288567 A1 | 9/2014 | Kroll |
| 2014/0324062 A1 | 10/2014 | Heuer et al. |
| 2015/0201972 A1 | 7/2015 | Doubler et al. |
| 2015/0201987 A1 | 7/2015 | Lemoine et al. |
| 2015/0250521 A1 | 9/2015 | Poker et al. |
| 2015/0359575 A1 | 12/2015 | Pech et al. |
| 2015/0374417 A1 | 12/2015 | Petit et al. |
| 2016/0022341 A1* | 1/2016 | Agarwal ............ A61B 17/7037 606/308 |
| 2016/0278815 A1 | 9/2016 | Fitzpatrick |
| 2016/0317206 A1 | 11/2016 | Rezach et al. |
| 2017/0119537 A1 | 5/2017 | Tepper et al. |
| 2017/0245898 A1 | 8/2017 | May et al. |
| 2018/0049777 A1 | 2/2018 | Rezach |
| 2018/0070941 A1 | 3/2018 | Zemlok et al. |
| 2018/0071000 A1 | 3/2018 | Pham et al. |
| 2018/0110548 A1 | 4/2018 | May et al. |
| 2018/0146990 A1 | 5/2018 | Manzanares et al. |
| 2018/0153600 A1 | 6/2018 | Koller et al. |
| 2018/0193062 A1 | 7/2018 | May |
| 2018/0193063 A1 | 7/2018 | May |
| 2018/0206890 A1 | 7/2018 | Rezach |
| 2018/0235684 A1 | 8/2018 | Hawkes et al. |
| 2018/0353224 A1 | 12/2018 | Kam et al. |
| 2019/0076170 A1 | 3/2019 | Lehman, Jr. et al. |
| 2019/0159820 A1 | 5/2019 | Geist et al. |
| 2019/0175193 A1 | 6/2019 | Fenn et al. |
| 2019/0254729 A1 | 8/2019 | Rohlfing et al. |
| 2019/0254730 A1 | 8/2019 | Rohlfing et al. |
| 2019/0329388 A1 | 10/2019 | Erickson et al. |
| 2019/0336187 A1 | 11/2019 | Zander et al. |
| 2019/0357948 A1 | 11/2019 | Wall et al. |
| 2019/0374263 A1 | 12/2019 | Wall et al. |
| 2020/0030015 A1 | 1/2020 | Grizzard et al. |
| 2020/0038064 A1 | 2/2020 | Stoklund et al. |
| 2020/0078056 A1 | 3/2020 | Biedermann et al. |
| 2020/0100817 A1 | 4/2020 | DiVincenzo et al. |
| 2020/0100824 A1 | 4/2020 | DiVincenzo et al. |
| 2020/0113603 A1 | 4/2020 | Simpson et al. |
| 2020/0121397 A1 | 4/2020 | Elliott et al. |
| 2020/0121398 A1 | 4/2020 | Elliott et al. |
| 2020/0205805 A1 | 7/2020 | Marks et al. |
| 2020/0229849 A1 | 7/2020 | Biedermann et al. |
| 2020/0237412 A1 | 7/2020 | Erramilli et al. |
| 2020/0340558 A1 | 10/2020 | Riemhofer et al. |
| 2020/0375638 A1 | 12/2020 | Avidano et al. |
| 2020/0390478 A1 | 12/2020 | Rodriguez et al. |
| 2020/0390486 A1 | 12/2020 | Rodriguez et al. |

FOREIGN PATENT DOCUMENTS

| | | |
|---|---|---|
| FR | 2827757 A1 | 1/2003 |
| JP | 2001252283 A | 9/2001 |

* cited by examiner

DORSAL ADJUSTING IMPLANT AND METHODS OF USE

CROSS-REFERENCE TO RELATED APPLICATIONS

This application incorporates by reference U.S. Pat. No. 10,335,201, titled Spinal Implant System and Methods of Use, filed Jan. 25, 2017; U.S. Pat. No. 10,653,455 titled Spinal Implant System and Methods of Use filed Sep. 12, 2017; U.S. Pat. No. 6,790,209, titled Rod Reducer Instruments and Methods, filed Jul. 1, 2002; U.S. application Ser. No. 17/167,258, titled Instrument for locking Orthopedic Screws, filed Feb. 4, 2021; and U.S. application Ser. No. 17/104,897, titled Combination Set Screw Breakoff and Tab Breaker Instrument, filed Feb. 3, 2021. The entire contents of each are incorporated herein by reference.

FIELD

The present disclosure generally relates to medical devices for the treatment of spinal disorders, and more particularly to a surgical implant system including a bone fastener and a related method. In various embodiments, an implant receiver may be secured to a pedicle screw and utilized to secure a rod within a cavity of the implant receiver. Moreover, a relative height of the rod within the cavity of the implant receiver may be adjusted during surgery in the dorsal direction without requiring that the rod be fully reduced relative to the implant receiver.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods, spinal constructs, and bone fasteners can be delivered to a surgical site. The rods may be attached via a spinal construct to the exterior of two or more vertebral members. This disclosure describes an improvement over these prior technologies.

SUMMARY

The techniques of this disclosure generally relate to a spinal implant system including an implant receiver that may be fixed to a pedicle screw and used to fix a longitudinally extending rod in a cavity of the implant receiver. A relative height of the rod may be adjusted in situ due to the inclusion of an adjustable nut on the outside of the implant receiver, for example.

In one aspect, the present disclosure provides for a spinal implant system. The spinal implant system may include an implant receiver having a base and a first arm and a second arm extending from the base in a longitudinal direction, for example. The first arm and second arm may define a receiving cavity extending between the first arm and second arm in the longitudinal direction from the base to an open end opposite the base, for example. In various embodiments, the first arm may have a first outside thread pattern extending in the longitudinal direction on an outside surface of the first arm and a first inside thread pattern extending in the longitudinal direction on an inside surface of the first arm, for example. In various embodiments, the second arm may have a second outside thread pattern extending in the longitudinal direction on an outside surface of the second arm and a second inside thread pattern extending in the longitudinal direction on an inside surface of the first arm, for example. In various embodiments a set screw may have a third outside thread pattern extending along an outside circumferential surface of the set screw having a size and shape corresponding to a size and shape of the first inside thread pattern and a size and shape of the second inside thread pattern, for example. In various embodiments, a nut may have a third inside thread pattern extending along an inside circumferential surface of the nut, and the third inside thread pattern may have a size and shape corresponding to a size and shape of the first outside thread pattern and a size and shape of the second outside thread pattern, for example.

In another aspect, the disclosure provides for a method of installing a spinal implant. The method may include the step of providing an implant receiver having a base and a first arm and a second arm extending in a longitudinal direction from the base to an open end, for example. In various embodiments, the first arm and second arm may define a receiving cavity extending between the first arm and second arm in the longitudinal direction from the base to the open end, for example. The method may further include the steps of securing the implant receiver to a bone screw, and reducing a rod to an intermediate elevation by pushing the rod through the open end into the receiving cavity, for example. In various embodiments, the intermediate elevation may be at any point between the base and the open end, for example. The method may further include the step of supporting the rod at the intermediate elevation.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1A:
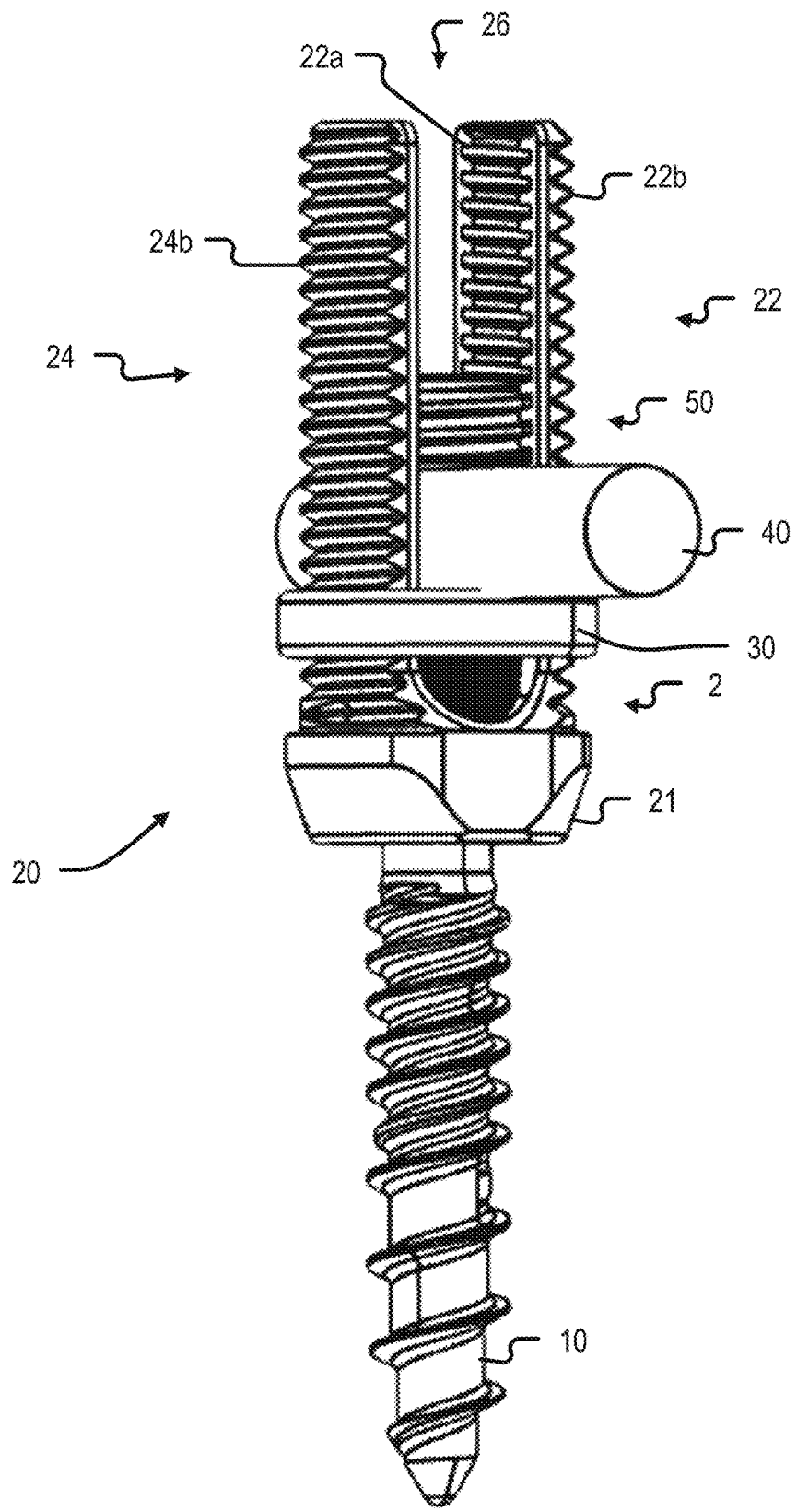
FIG. 1A is a perspective view of a spinal implant system.

Embodiments of the present disclosure relate generally, for example, to spinal stabilization systems, and more particularly, to surgical instruments for use with spinal stabilization systems. Embodiments of the devices and methods are described below with reference to the Figures.

The following discussion omits or only briefly describes certain components, features and functionality related to medical implants, installation tools, and associated surgical techniques, which are apparent to those of ordinary skill in the art. It is noted that various embodiments are described in detail with reference to the drawings, in which like reference numerals represent like parts and assemblies throughout the several views, where possible. Reference to various embodiments does not limit the scope of the claims appended hereto because the embodiments are examples of the inventive concepts described herein. Additionally, any example(s) set forth in this specification are intended to be non-limiting and set forth some of the many possible embodiments applicable to the appended claims. Further, particular features described herein can be used in combination with other described features in each of the various possible combinations and permutations unless the context or other statements clearly indicate otherwise.

Terms such as "same," "equal," "planar," "coplanar," "parallel," "perpendicular," etc. as used herein are intended to encompass a meaning of exactly the same while also including variations that may occur, for example, due to manufacturing processes. The term "substantially" may be used herein to emphasize this meaning, particularly when the described embodiment has the same or nearly the same functionality or characteristic, unless the context or other statements clearly indicate otherwise.

Referring to FIGS. 1-10 generally, various spinal implant systems 100 are disclosed. The components of spinal implant system 100 can be fabricated from biologically acceptable materials suitable for medical applications, including metals, synthetic polymers, ceramics and bone material and/or their composites. For example, the components of spinal implant system 100, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 100 may have material composites, including the above materials, to achieve various desired characteristics such as strength, rigidity, elasticity, compliance, biomechanical performance, durability and radiolucency or imaging preference. The components of spinal implant system 100, individually or collectively, may also be fabricated from a heterogeneous material such as a combination of two or more of the above-described materials, for example. The components of spinal implant system 100 may be monolithically formed, integrally connected or include fastening elements and/or instruments, as described herein.

Figure 1B:
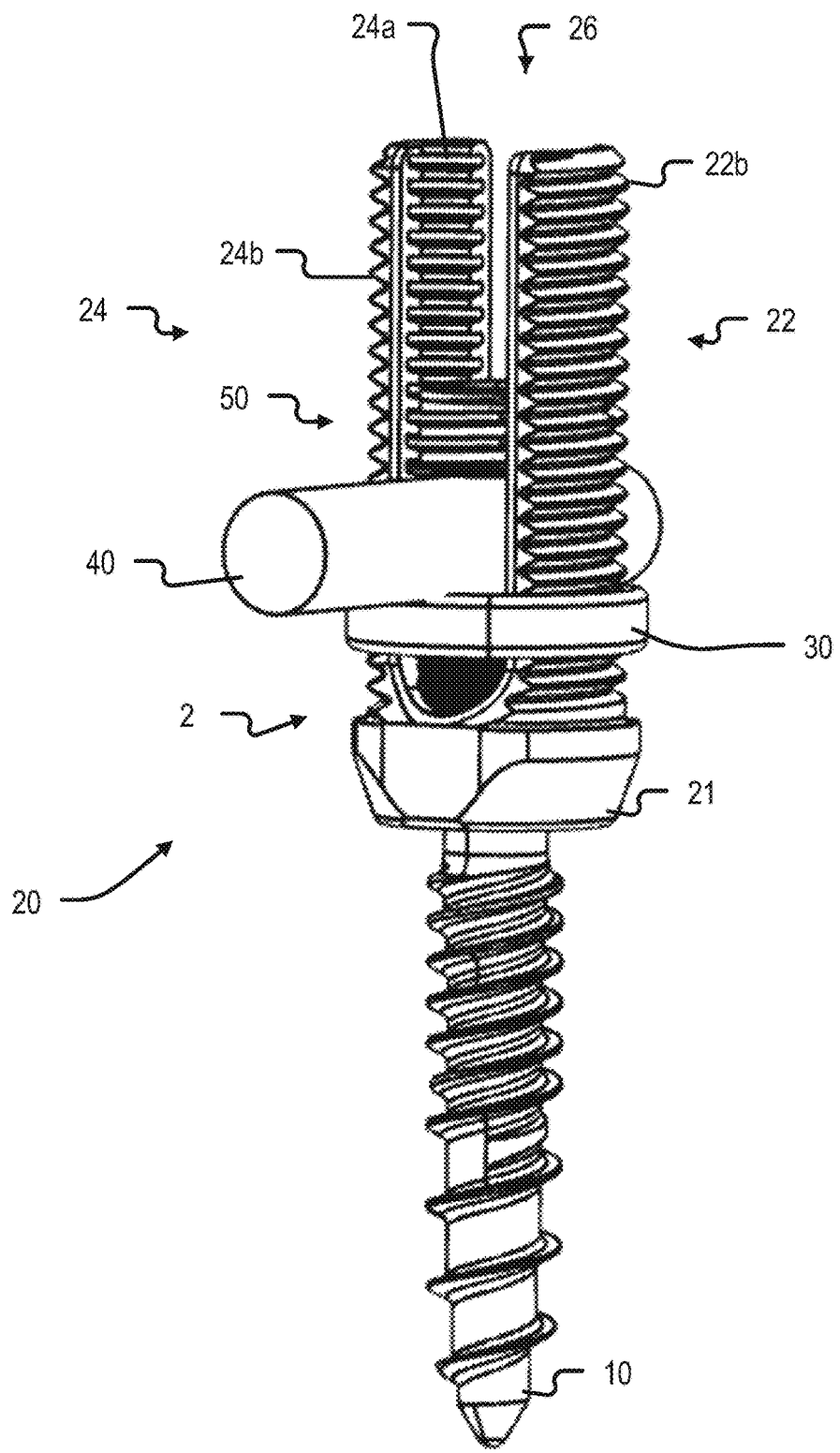
FIG. 1B is an alternate perspective view of a spinal implant system.
Figure 1C:
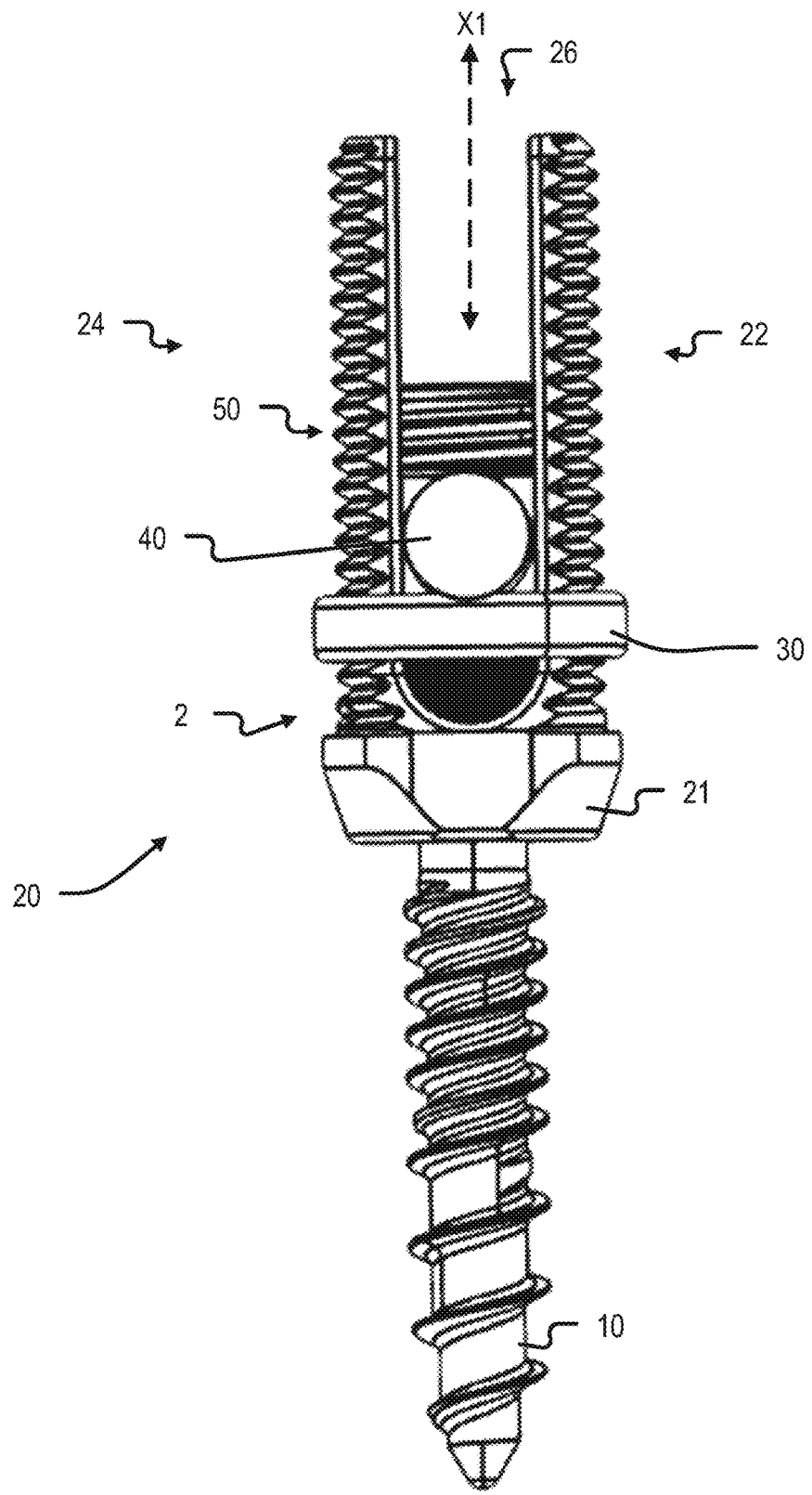
FIG. 1C is a head on view of a spinal implant system.

Referring to FIGS. 1A-1C various views of a spinal implant system 100 are illustrated. Spinal implant system 100 may include an implant receiver 20 having a first arm 22 and a second arm 24 defining a receiving cavity 26 therebetween, for example Implant receiver 20 may have a base portion 21 including a lower cavity therein for securely attaching to a bone screw 10, for example a pedicle screw secured to a vertebrae of a patient. Various examples of how the implant receiver 20 may be securely attached to a bone screw 10 will be explained in further detail below. Additional examples of how an implant receiver 20 may securely connect to a bone screw 10 via an internal cavity of base portion 21 and are also disclosed in detail in each of U.S. Pat. No. 10,335,201, titled Spinal Implant System and Methods of Use; and U.S. Pat. No. 10,653,455 titled Spinal Implant System and Methods of Use; U.S. application Ser. No. 17/167,258, titled Instrument for locking Orthopedic Screws, which are all incorporated herein by reference in their entireties.

The first and second arms 22, 24 may extend in a parallel direction to axis Xi (see FIG. 1C), for example an axis extending longitudinally through the center of implant receiving cavity 26 and the base portion of implant receiver 20. Axis $X_1$ may be aligned with an extension direction of bone screw 10 as illustrated herein, although in some embodiments implant receiver 20 may also be inclined about +/−30 degrees with respect to an extension direction of bone screw 10. For example, implant receiver 20 may be a multiaxial receiver capable of securely attaching to multiaxial bone screw 10 in any inclined orientation relative to an extension direction of bone screw 10. In some embodiments, bone screw 10 may be configured as multi-axial screws, sagittal angulation screws, pedicle screws, mono-axial screws, uni-planar screws, fixed screws, anchors, tissue penetrating screws, conventional screws, expanding screws. In some embodiments, bone screw 10 may be employed with wedges, anchors, buttons, clips, snaps, friction fittings, compressive fittings, expanding rivets, staples, nails, adhesives, posts, connectors, fixation plates and/or a post, to name a few possible example configurations.

Spinal implant system 100 may include a nut 30, which may move upward and downward in a direction parallel to axis $X_1$ by rotating nut 30 clockwise and/or counterclockwise. Nut 30 may provide a lower support for a rod 40, for example. Although rod 40 is shown as a relatively short straight section, rod 40 may be a longitudinally extending rod that extends through receiving cavity 26 and may be bent and/or curved at portions thereof on the outside of receiving cavity 26 according to the particular needs of a surgeon and a patient specific surgical plan, for example. Rod 40 may be secured against nut 30 by a set screw 50 disposed within receiving cavity 26, for example Set screw 50 may move upward and downward in a direction parallel to axis Xi by rotating set screw 50 clockwise and/or counterclockwise. In various embodiments, set screw 50 may be a breakoff setscrew having a breakoff portion 52 (see FIG. 2) or set screw 50 may be a solid setscrew without a breakoff portion.

First arm 22 and second arm 24 may each include an outside curved surface and an interior curved surface that each have thread patterns extending along the length thereof. For example, first arm 22 may have a first exterior thread pattern 22b extending on the outside curved surface thereof and second arm 24 may have a second exterior thread pattern 24b extending on the outside curved surface thereof. The timing and/or pitch of the first external thread pattern 22b may correspond in size and shape to the timing and/or pitch of the second external thread pattern 24b, for example. Additionally, it should be understood that the timing and/or pitch of the first and second external thread patterns 22b, 24b may take into account the void space between arms 22, 24 such that the discontinuity between thread patterns 22b, 24b picks up at an appropriate location and/or is accounted for such that nut 30 may seamless rotate around both of first and second arms 22, 24 along first and second external thread patterns 22b, 24b. Similarly, first arm 22 may have a first interior thread pattern 22a extending on the interior curved surface thereof and second arm 24 may have a second interior thread pattern 24a extending on the interior curved surface thereof. The timing and/or pitch of the first internal thread pattern 22a may correspond in size and shape to the timing and/or pitch of the second internal thread pattern 24a, for example. Additionally, it shall be understood that the timing and/or pitch of the first and second external thread patterns 22b, 24b may take into account the void space between arms 22, 24 such that the discontinuity between thread patterns 22a, 24a, picks up at an appropriate location and/or is accounted for. Furthermore, in various embodiments, the major diameter of first and second interior thread patterns 22a, 24a may be timed with the minor diameter of the first and second exterior thread patterns 22b, 24b. For example, they may be at the same or substantially the same elevation of arms 22, 24. This timing may result in a configuration where the cross sectional thickness through arms 22, 24 is relatively thin at the corresponding locations where the major diameter of first and second interior thread patterns 22a, 24a is at substantially the same elevation as the minor diameter of the first and second exterior thread patterns 22b, 24b. This corresponding relationship may create a plurality of sequentially stacked shear planes in the first arm 22 and second arm 24, respectively, as will be explained in more detail below in conjunction with FIGS. 8A and 8B as breakoff portions.

In various embodiments, the first and second exterior thread patterns 22b, 24b may configured to rotatably support nut 30, and nut 30 may have an interior thread pattern 31 (see FIG. 2) having a timing and/or pitch including a size and shape generally corresponding to the first and second exterior thread patterns 22b, 24b, for example. For example still, a first interior diameter may be defined by the interior curved surface of arms 22, 24 and setscrew 50 may have a first exterior diameter corresponding in length to the first interior diameter. Similarly, in various embodiments, the first and second interior thread patterns 22a, 24a may be configured to rotatably support set screw 50, and set screw 50 may have an exterior thread pattern 51 (see FIG. 2) having a timing and/or pitch including a size and shape generally corresponding to the first and second interior thread patterns 22a, 24a, for example. For example still, a second exterior diameter may be defined by the exterior curved surfaces of arms 22, 24 and nut 30 may have a second interior diameter corresponding in length to the second exterior diameter. Set screw 50 may include a drive end 53. Drive end 53 may take any shape, for example a hexalobular shape, a hexaganol shape, a torx shape, etc.

Figure 2A:
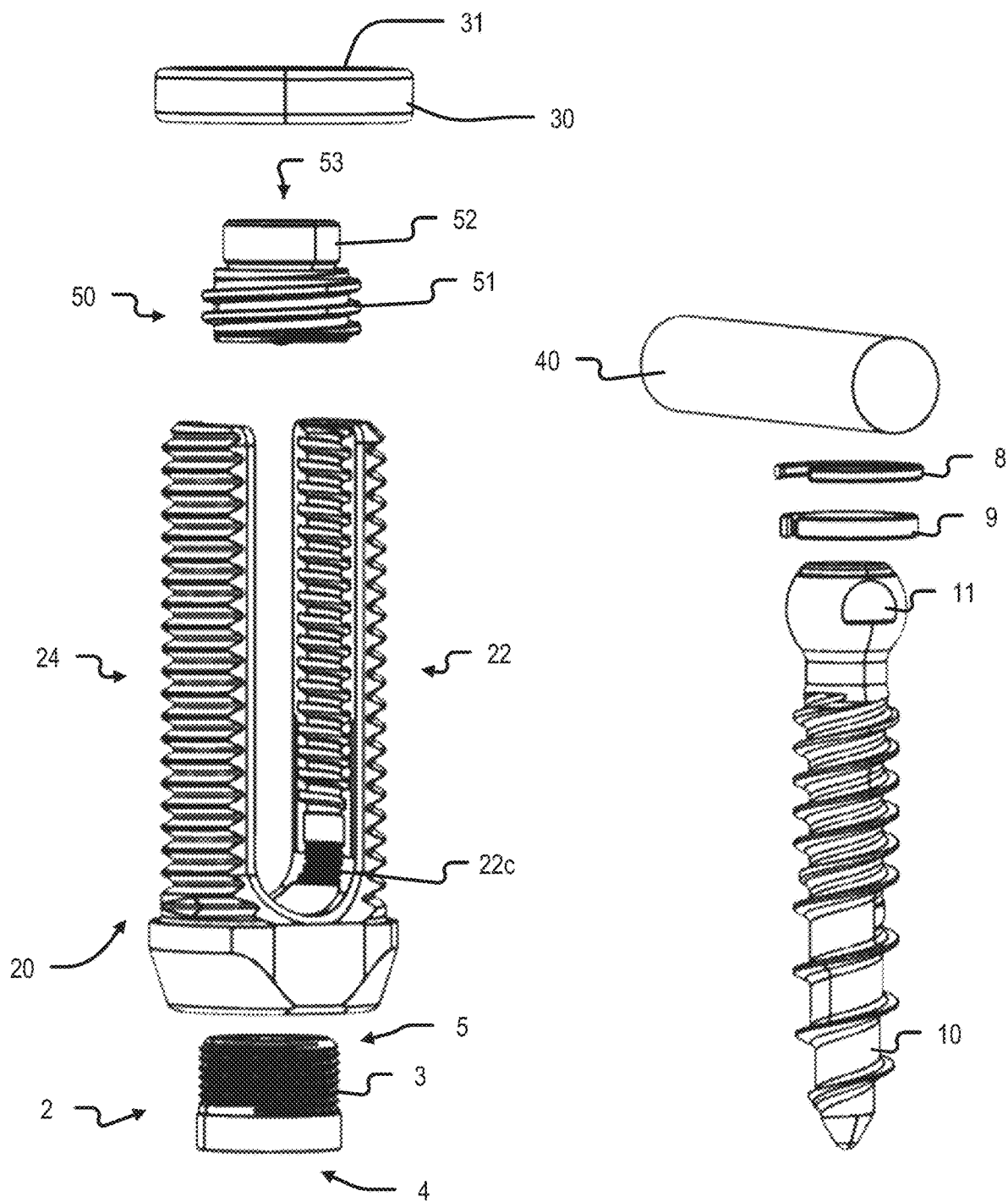
FIG. 2A is a first exploded parts view of a spinal implant system.
Figure 2B:
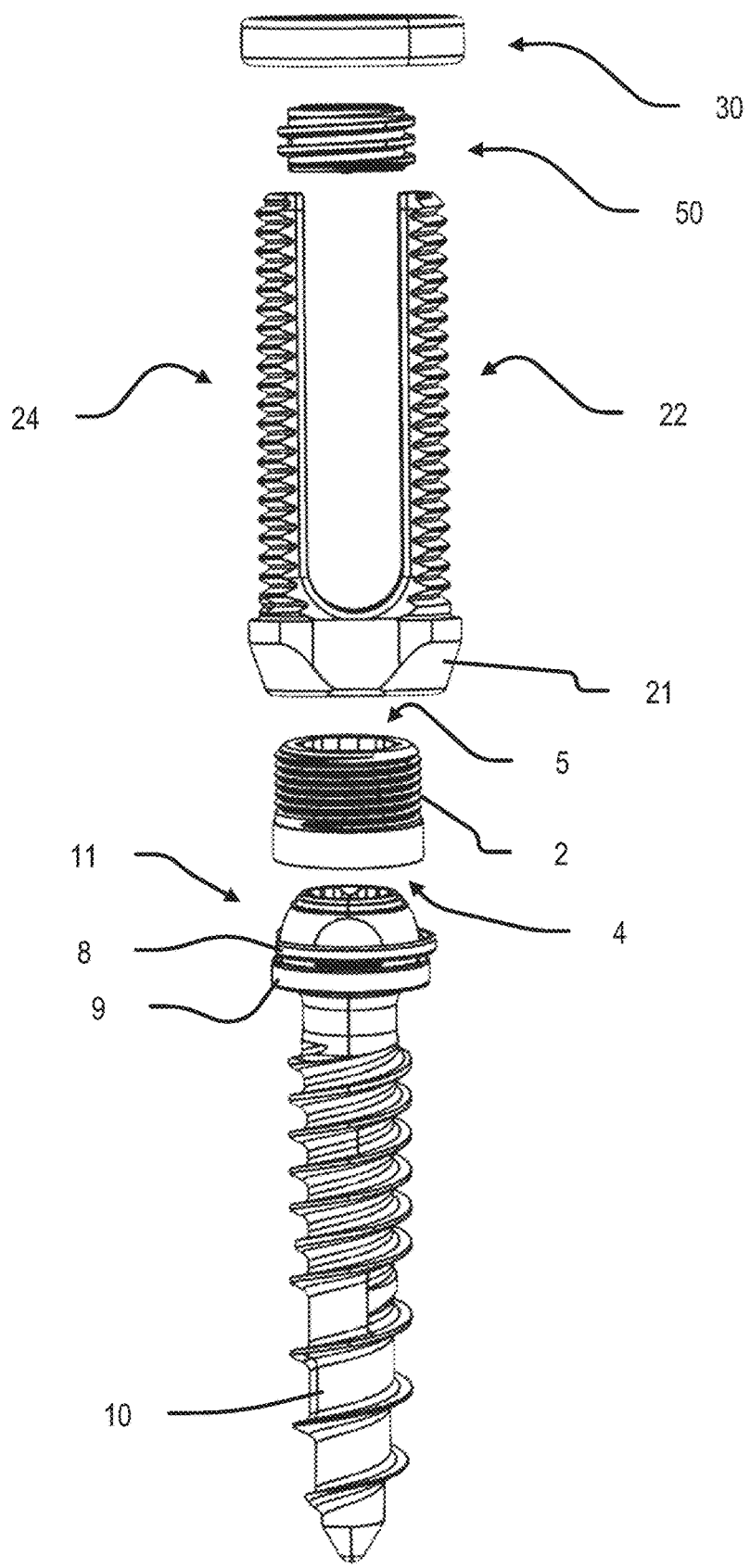
FIG. 2B is a second exploded parts view of a spinal implant system.

FIGS. 2A-2B are various exploded parts views of a spinal implant system 100. Spinal implant system 100 may include an implant receiver 20, a rotatable nut 30, and a breakoff set screw 50, for example. Implant receiver 20 may be configured to securely couple to bone screw 10. Bone screw 10 may be a multiaxial bone screw, for example Spinal implant system 100 may include a crown 2 having an external thread pattern 3 extending along the outside circumferential surface thereof and a head receiving cavity 4 for seating the head portion 11 of a bone screw 10 therein, for example. The external thread pattern 3 of crown 2 may be engaged with lower interior thread patterns 22c, 24c of first and second arms 22, 24, for example. In some embodiments, the lower interior thread patterns 22c, 24c may be inset towards axis $X_1$ relative to interior thread patterns 22a, 22b, for example. Crown 2 may also include a drive end 5 having an engagement aperture for engaging with a driver and rotating crown 2 within lower interior thread patterns 22c, 24c (see also FIG. 4) to fix implant receiver 20 to bone screw 10, for example Drive end 5 may take any shape, for example a hexalobular shape, a hexaganol shape, a torx shape, etc. Spinal implant system 100 may include an upper ring 8 and a lower ring 9. Upper and lower rings 8, 9 may be C-shaped and configured to securely couple head portion 11 of bone screw 10 within lower cavity of base portion 21, for example. As shown best in FIG. 2B, the upper and lower rings 8, 9 are shown connected to head portion 11 of bone screw 10, for example.

Figure 3:
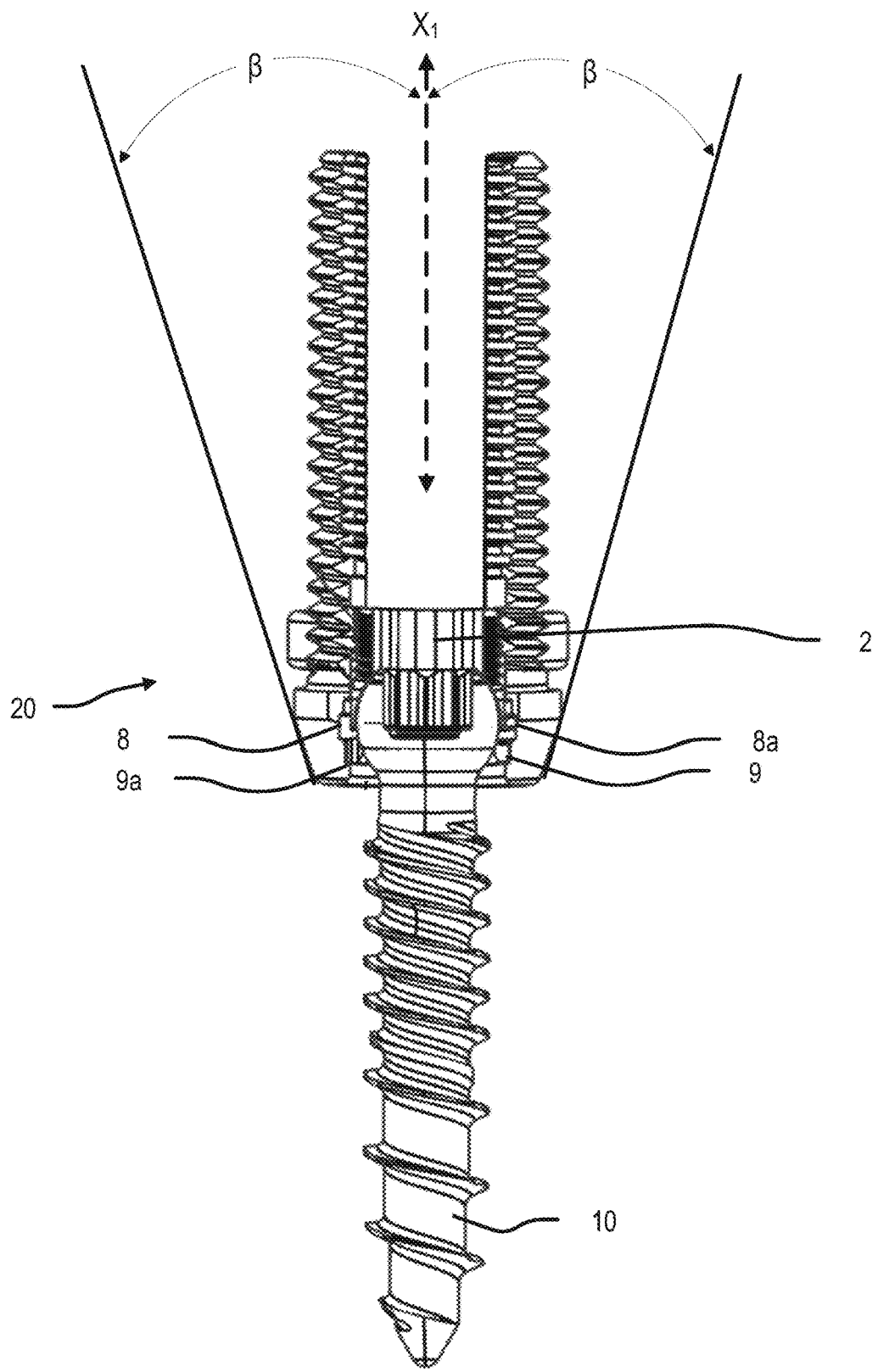
FIG. 3 is a front view cross section of a spinal implant system in a first configuration.

FIG. 3 is a front view cross section of a spinal implant system 100 in a first configuration where the implant receiver 20 is securely coupled to bone screw 10 at a desired angle. For example, a surgeon may initially couple the implant receiver 20 to bone screw 10 by pushing implant receiver 20 down against the bone screw 10 by, e.g., an instrument for locking orthopedic screws. For example, a surgical instrument may push implant receiver 20 down such that the upper and lower rings 8, 9 are seated around the head portion 11 of bone screw 10 and nested within and retained by corresponding cavities 8a, 9a of base portion 21, for example. In seating upper and lower rings 8, 9 in corresponding cavities 8a, 9a implant receiver 20 may be secured to bone screw 10. Additionally, in various multi-axial embodiments, initially implant receiver 20 may be inclinable +/−by a degree β relative to an extension direction (longitudinal direction) of bone screw 10, for example. In some embodiments, β may be about +/−30 degrees and in at least one embodiment β may be about 26 degrees, for example Once a surgeon has positioned implant receiver 20 at an appropriate angle relative to bone screw 10, the surgeon may tighten crown 2 down to secure implant receiver 20 in the desired angular orientation, for example. As shown in FIG. 3, and for ease in understanding, spinal implant system 100 is secured in a substantially vertical direction where axis $X_1$ may be considered coincident with an axis defined by an extension direction of bone screw 10, for example. In this way, spinal implant system 100 is securely fixed to bone screw 10 in a desired angular orientation.

Figure 4:
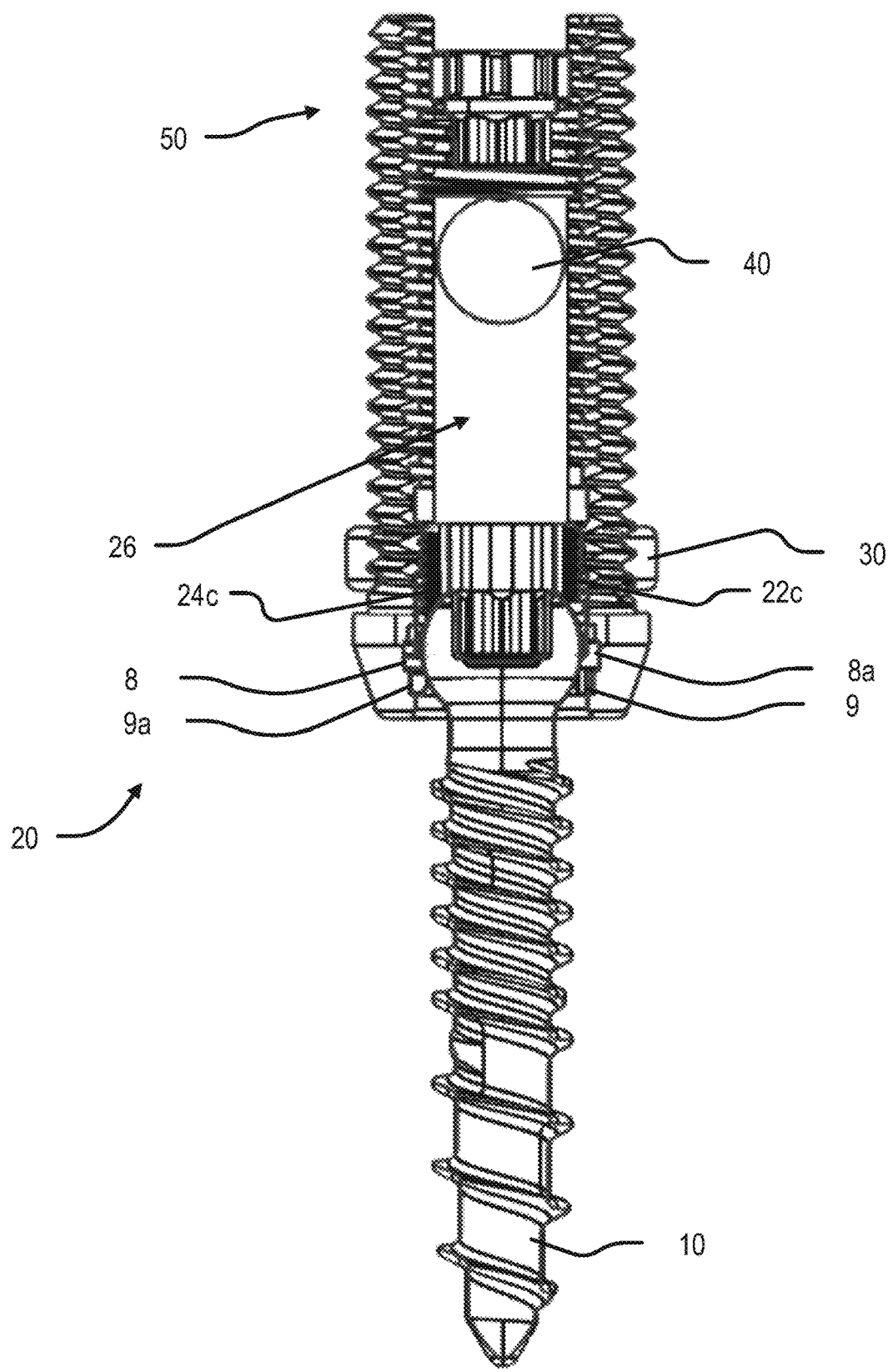
FIG. 4 is a front view cross section of a spinal implant system in a second configuration.
Figure 5:
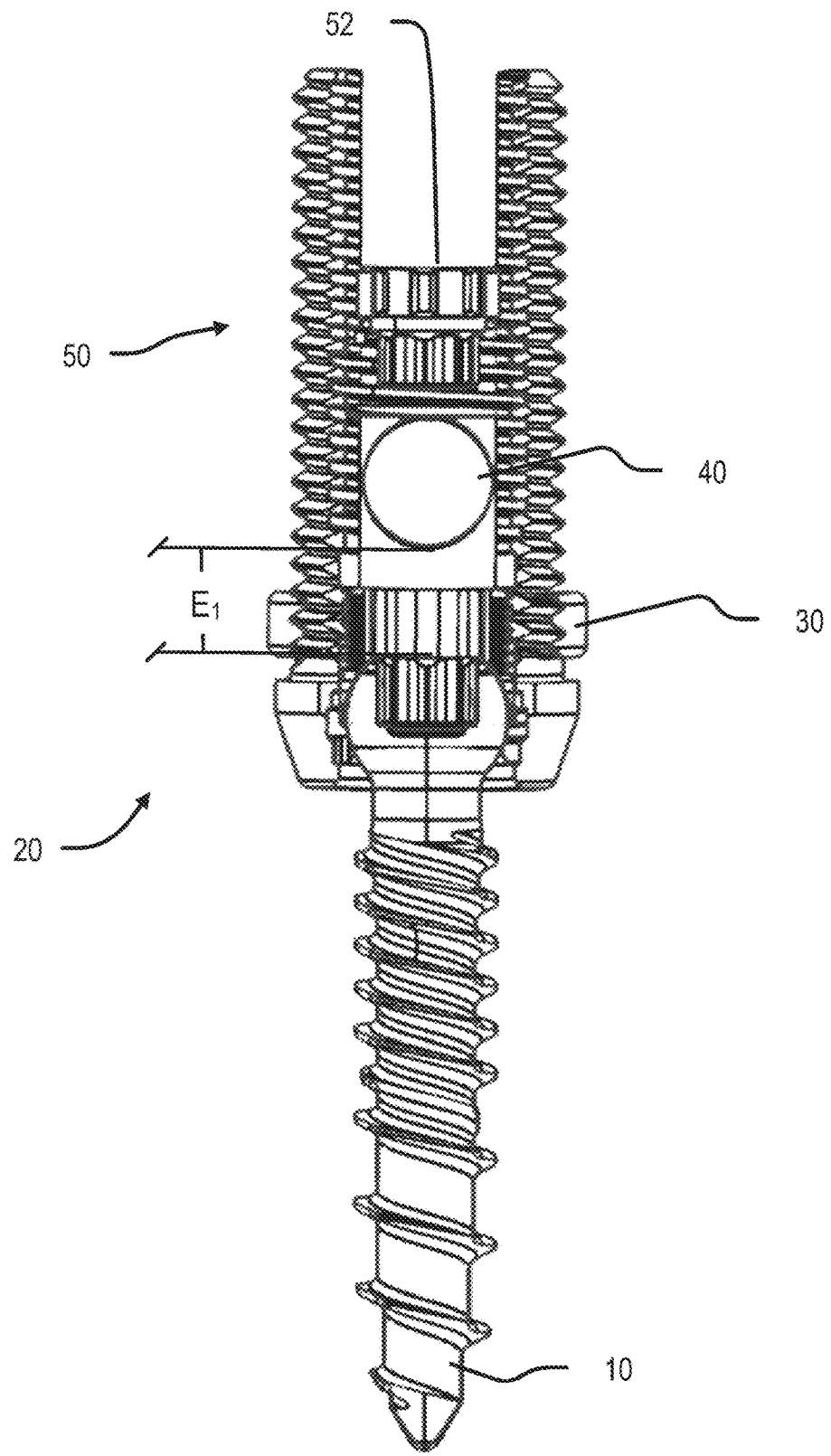
FIG. 5 is a front view cross section of a spinal implant system in a third configuration.

FIG. 4 is a front view cross section of a spinal implant system 100 in a second configuration. In the second configuration, a surgeon may position rod 40 within implant receiving cavity 26. A surgeon may elect to reduce rod 40 within receiving cavity 26 to a desired height with a rod-reducing instrument. For example, the rod-reducing instrument described in U.S. Pat. No. 6,790,209, titled Rod Reducer Instruments and Methods, the entire contents of which are incorporated herein in their entirety. As shown in FIG. 5, spinal implant system 100 is in a third configuration where a surgeon may have reduced rod 40 to an elevation $E_1$ that the surgeon is comfortable with. For example, in some instances, and particularly in complex deformation surgeries, a surgeon may only feel comfortable initially reducing rod 40 to a height that is relatively high above the head of bone screw 10. For example a height that is not fully reduced towards bone screw 10 at elevation $E_1$. For example, a surgeon may sense when to stop further reducing rod 40 due to tactile feedback, experience, and various types of nerve monitoring. At least one reason the surgeon may not want to reduce rod 40 further down towards bone screw 10 is a concern that the force may be too great and pull bone screw 10 out of the patient's anatomy (e.g., a boney structure such as a vertebrae). This may be a particularly important consideration in select surgeries where a patient's vertebrae may be degraded, diseased, and/or relatively week from prior surgeries and/or injuries, for example. This also may be particularly advantageous when securing a longitudinal rod 40 spanning a length of a human spine that is secured via multiple spinal implant systems 100. For example, rod 40 may be incrementally brought down towards each of the various bone screws 10 within each of the various implant receiving cavities 26 incrementally and/or in sequence and at different relative elevations. The top loading configuration of spinal implant system 100 may also facilitate a sequential loading as described above.

Figure 6:
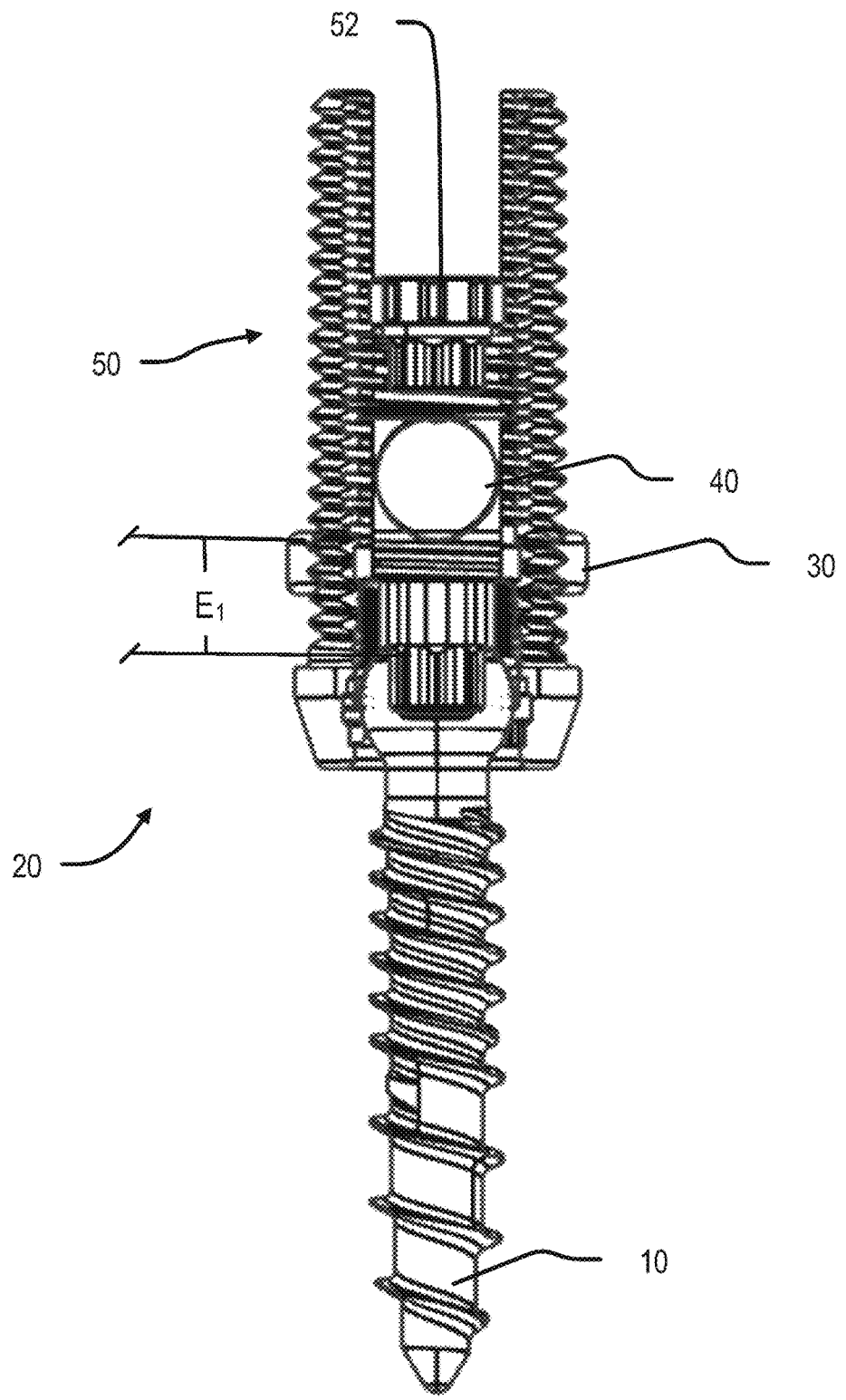
FIG. 6 is a front view cross section of a spinal implant system in a fourth configuration.
Figure 7:
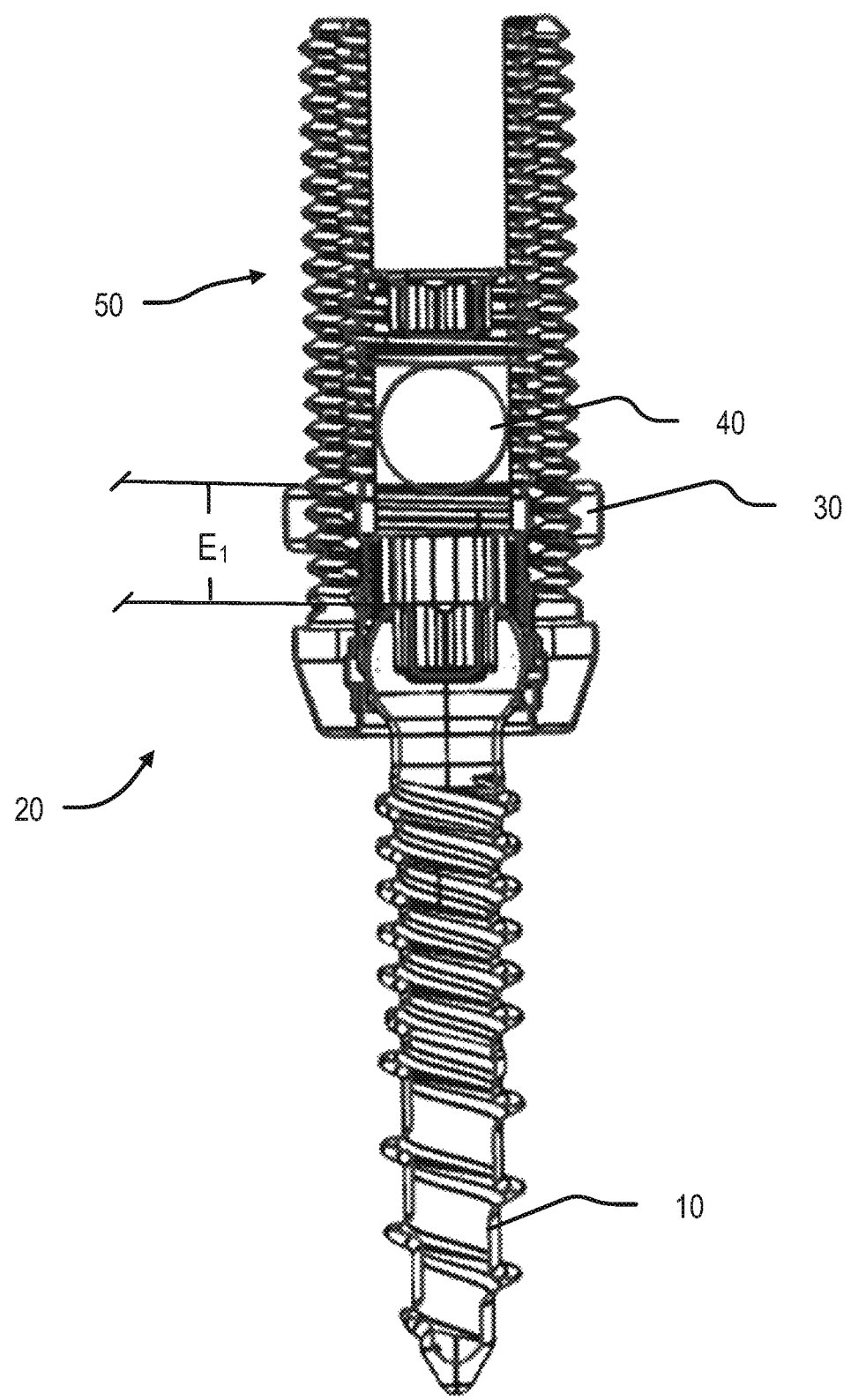
FIG. 7 is a front view cross section of a spinal implant system in a fifth configuration.

FIG. 6 is a front view cross section of a spinal implant system 100 in a fourth configuration. In the fourth configuration, a surgeon may rotate nut 30 around exterior thread patterns 22b, 24b such that nut 30 is linearly translated upward towards rod 40. In the example embodiment, nut 30 provides a bearing surface to support rod 40. For example, an upper surface of nut 30 is in direct contact with a lower surface of rod 40. At this stage, a surgeon may further tighten set screw 50 to press against (compress and/or urge) rod 40 such that interior threads 31 of nut 30 are tightened against the exterior thread patterns 22b, 24b in the vertical direction, for example. In doing so, the nut 30 may become locked at a relative location due to the force applied by set screw 50 to rod 40, for example FIG. 7 is a front view cross section of a spinal implant system in a fifth configuration. In the fifth configuration, a surgeon may have broken off the breakoff portion 52 of the set screw 50. For example, the surgeon may be satisfied with the location of rod 40 at the desired elevation $E_1$. A surgeon may break off the breakoff portion 52 by shearing the breakoff portion 52 with a surgical instrument (not illustrated). For example, an instrument such as the various embodiments described in U.S. application Ser. No. 17/104,897, titled Combination Set Screw Breakoff.

Figure 8A:
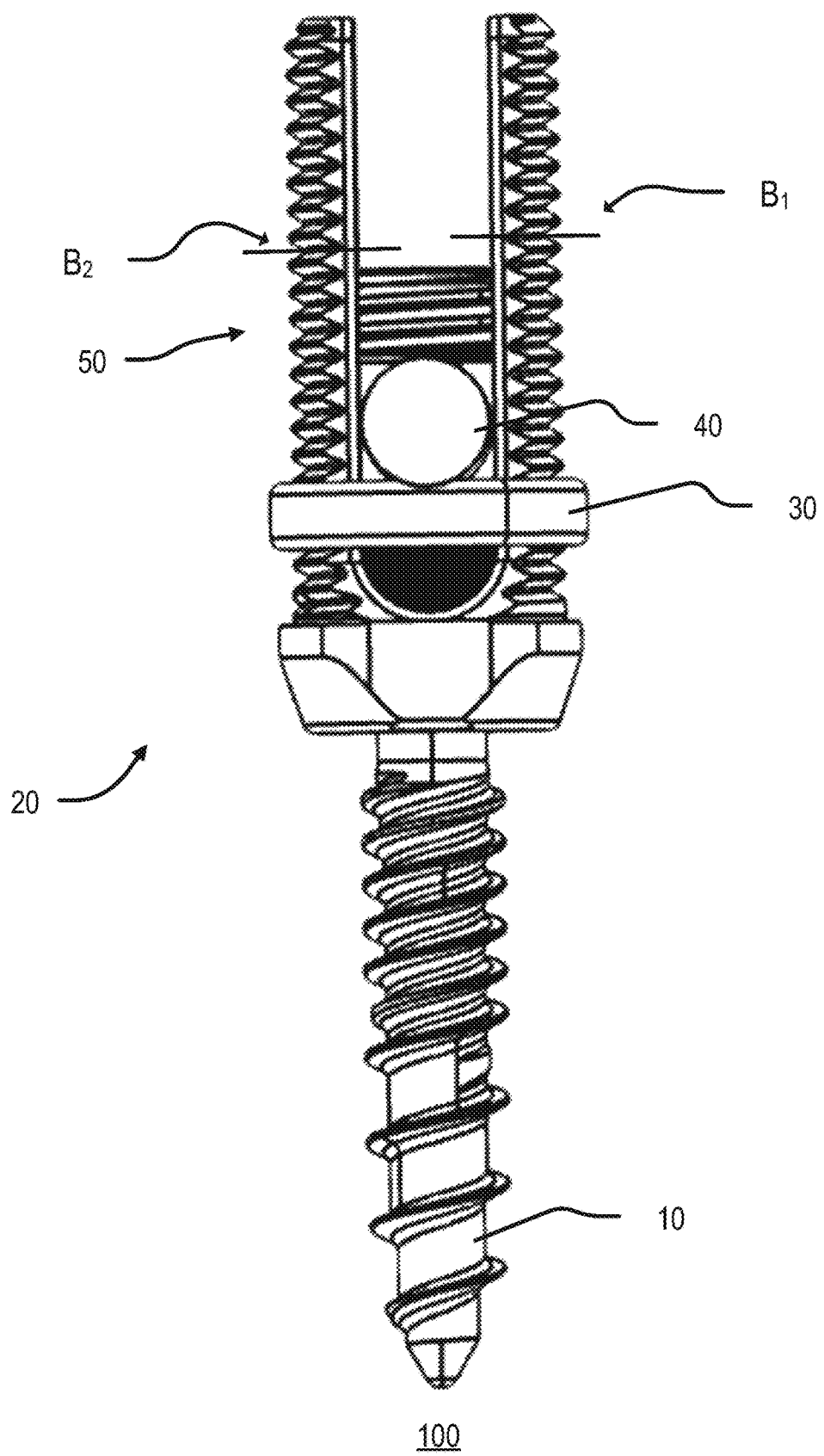
FIG. 8A is a front view of a spinal implant system after a breakoff portion of a breakoff set screw has been severed.
Figure 8B:
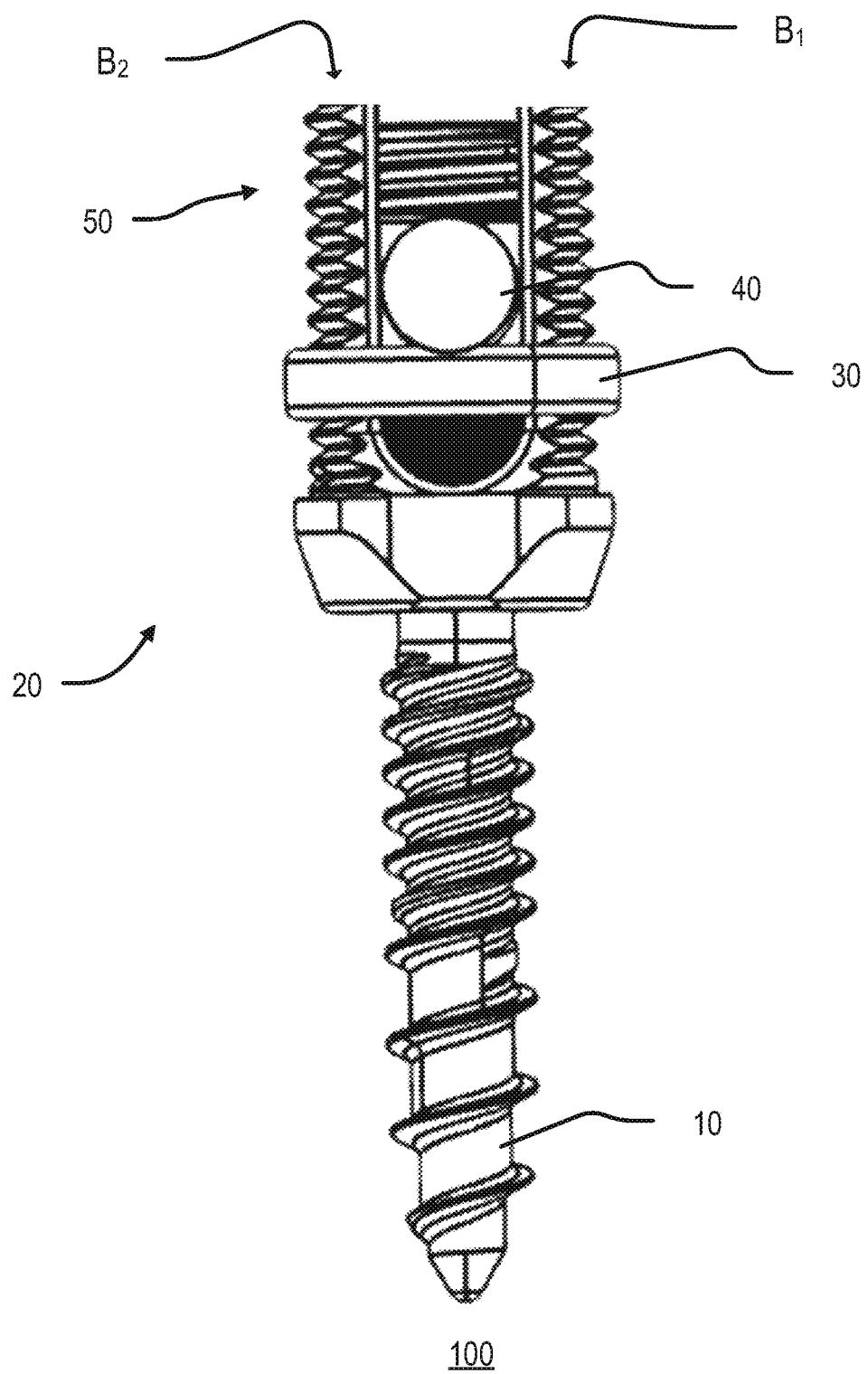
FIG. 8B is a front view of a spinal implant system after left and right break off tabs of an implant receiver have been severed.

FIG. 8A is a front view of a spinal implant system after a breakoff portion 52 of a breakoff set screw 50 has been severed. As illustrated, nut 30 is secured in place and supports rod 40 at an elevation $E_1$ that is above the head portion of bone screw 10 and/or the lowermost viable portion of receiving cavity 26. As should be understood, nut 30 may support rod 40 at any one of a plurality of different elevations between base 21 and an open end of the receiving cavity 26, for example. In this configuration, the relative location of set screw 50, nut 30, and rod 40 is fixed relative to implant receiver 20. As illustrated, the first arm 24 and second arm 22 extend beyond the top of set screw 50. Accordingly, a surgeon may break off the portions of first arm 22 and second arm 24 that extend beyond the top of set screw 50 at breakoff locations $B_1$, $B_2$ with, for example, a breakoff instrument such as the various embodiments described in U.S. application Ser. No. 17/104,897, titled Combination Set Screw Breakoff. As explained above, breakoff locations breakoff locations $B_1$, $B_2$ may correspond to a shear plane where the cross sectional thickness of arms 22, 24 is thinnest. For example, where the major diameter of first and second interior thread patterns 22a, 24a is at substantially the same elevation as the minor diameter of the first and second exterior thread patterns 22b, 24b.

Figure 9:
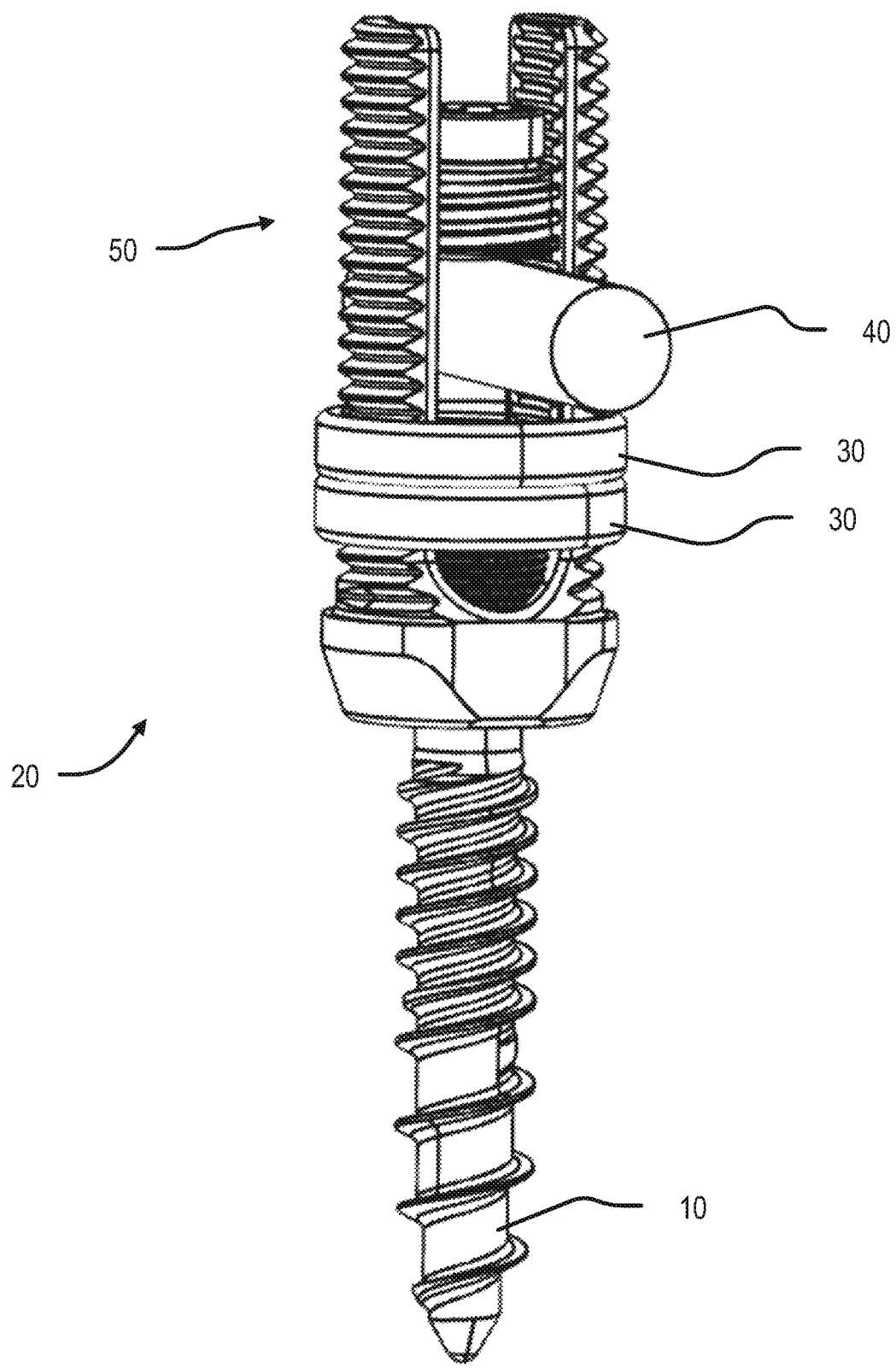
FIG. 9 is a perspective view of a spinal implant system including two frictionally engaged nuts.

FIG. 9 is a perspective view of a spinal implant system 100 including two frictionally engaged nuts 30. In the example embodiment, a first nut 30 and a second nut 30 are provided below rod 40. At least one advantage of providing a first nut 30 and a second nut 30 is to facilitate jamming of the nuts 30 such that nuts 30 are prevented and/or suppressed from rotating. For example, the first nut 30 and second nut 30 are in direct contact with one another and are frictionally engaged at the respective contact surfaces.

Figure 10:
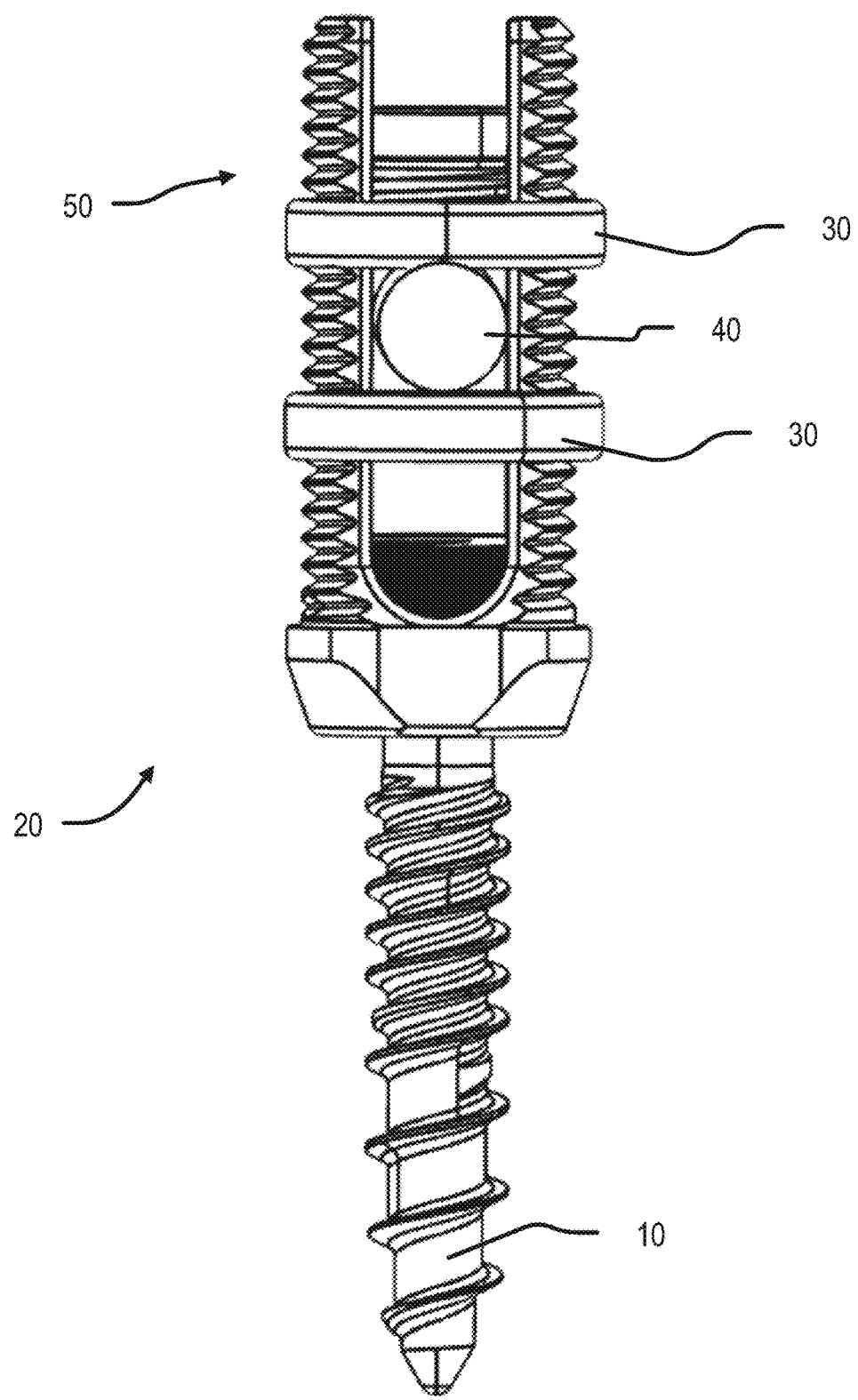
FIG. 10 is a perspective view of a spinal implant system including a top nut and a bottom nut.

FIG. 10 is a perspective view of a spinal implant system 100 including a top nut 30 and a bottom nut 30. Top nut 30 may provide a circumferential retaining force preventing the upper portions of arms 22, 24 from bowing outward laterally and/or splaying while tightening set screw 50, for example. In some embodiments, top nut 30 may be temporarily installed above rod 40 while breaking off the breakoff portion 52 of set screw 50 and or breaking off the upper tab portions of first arm 22, and/or second arm 24, for example. Thereafter, nut 30 may be removed. Alternatively, top nut 30 may remain installed with spinal implant system 100 depending on a surgeon's preference.

Figure 11:
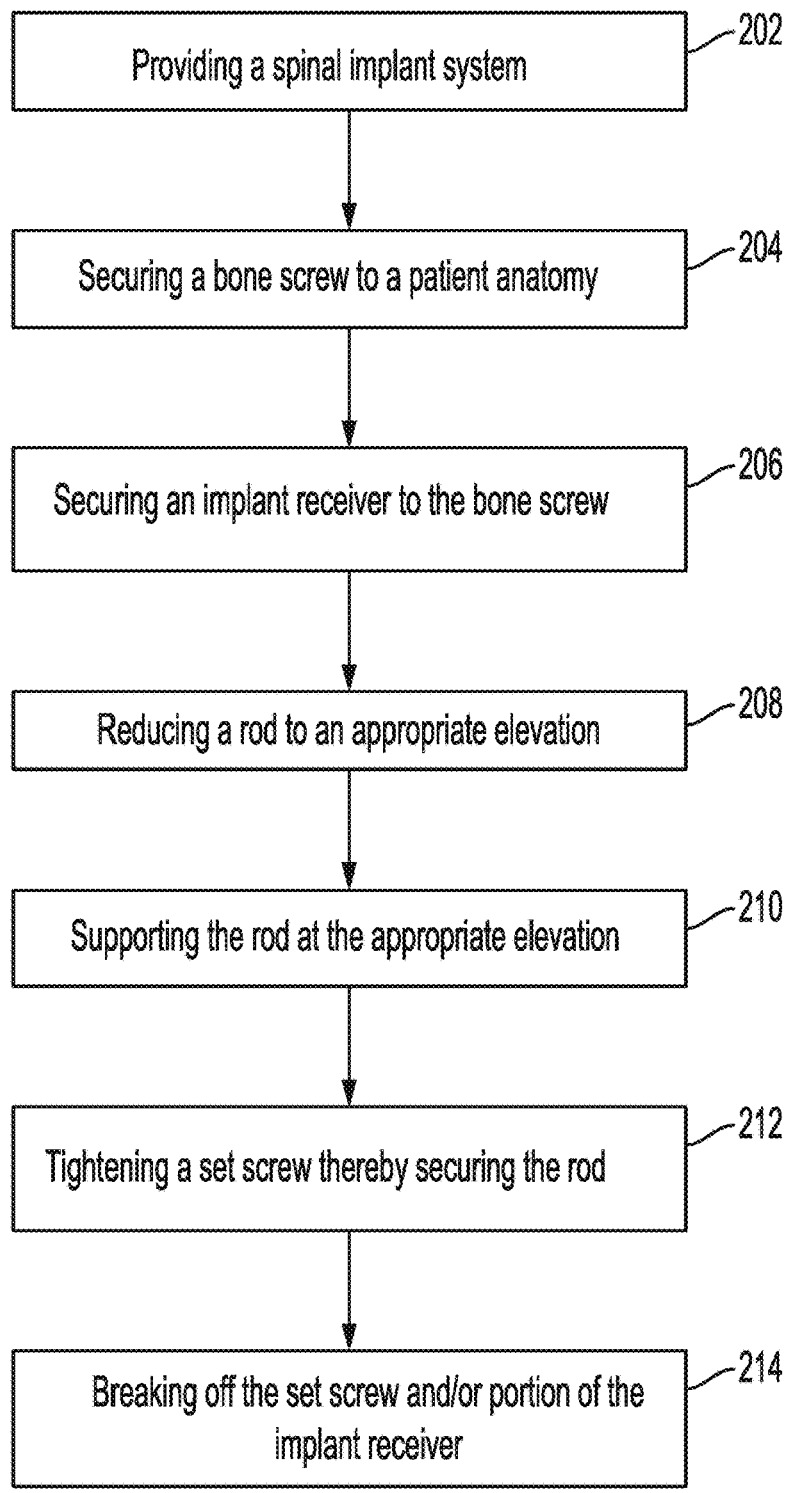
FIG. 11 is a flow chart of an example method of use of disclosed spinal implant embodiments.

FIG. 11 is an example flow chart of a method 200 of installation of example embodiments disclosed herein. The following discussion of method 200 may include reference to components, features, and functionality of spinal implant system 100 as explained above for context, however, the method as disclosed below is not limited to the specific spinal implant system 100 embodiments disclosed above. At step 202, a spinal implant system may be provided, for example spinal implant system 100 or the like. At step 204, a bone screw 10 or fastener may be secured to a patient's anatomy, for example bone screw 10 may be secured to a patient vertebrae. At step 206, an implant receiver of the spinal implant system 100 may be secured to the bone screw 10. For example, implant receiver 20 may be securely coupled to bone screw 10 by pushing implant receiver 20 downward and seating various locking rings 8, 9 around a head portion of bone screw 10 and within various receiving cavities 8a, 9a, of implant receiver 20 as explained above.

Step 206 may also include the step of tightening a crown 2 on top of bone screw 10 to secure the orientation of implant receiver 20. For example, an angle of implant receiver relative to bone screw 10 may be fixed by tightening the crown 2 against the bone screw 10. At step 208, a rod 40 may be reduced within a receiving cavity of an implant receiver 20 to an appropriate elevation. For example, a rod reduction tool may reduce a rod 40 to any elevation within the receiving cavity of implant receiver. For example still, a surgeon can push downward on the rod with their hands and/or fingers. Furthermore, and as another example, a surgeon can also push downward on the rod by rotating the set screw and advancing the rod downward due to the downward pushing force of the set screw. Similarly, in some embodiments, a second nut may be on top of the rod and the second nut can also push downward on the rod to assist with reducing the rod in the implant cavity.

In some embodiments, the rod 40 may be reduced to an intermediate elevation relatively high above the head of bone screw that is above the lowermost point rod 40 may be reduced to. For example, a "target elevation" of the rod may be known, and the rod may be reduced to the target elevation by any of the above noted procedures and their equivalents, alone or in any combination. Furthermore, in some procedures, a surgeon may want to raise the rod upward after the reducing step(s) as explained above in the event the rod is reduced to far or other co-related surgical steps call for the rod being at a higher elevation or lower elevation during an intermediate portion of the surgery. In those instances, a surgeon could rotate the bottom nut supporting the rod to raise the rod back upward in the vertical direction and/or downward depending on the particular needs of the surgeon. At step 210, the rod 40 may be supported at an appropriate elevation established at step 208. For example, nut 30 may be rotated around the outside threaded surface of implant receiver 20 thereby moving nut 30 upwards in a position to support rod 40. At step 212, a set screw 50 disposed in the implant receiving cavity above rod 40 may be tightened. By tightening set screw 50, the rod 40 may be pushed against the nut 30 and held in place. At step 214, a portion of set screw 50 may be broken off, for example breakoff portion 52. Additionally, in some embodiments an upper portion of the arms 22, 24 of implant receiver 20 may be broken off at any location amongst a plurality of breakoff locations. In some surgical procedures, it is envisioned that a surgeon may use a lower nut to raise the whole construct and the vertebral body the bone screw is secured to. For example, once the rod is secured in place relatively firmly against the set screw, a surgeon may rotate the lower nut in an appropriate direction which in turn causes an upward pushing force against the rod. Provided the rod is secured on at least one opposite end, by rotating the nut the boney anatomy that the bone screw is secured to will also experience an upward pulling force due to the nut pushing the rod upward and the rod being constrained within the receiving cavity relative to the construct. In doing so, this method may raise a corresponding vertebral body, thereby assisting a surgeon with aligning the target vertebrae in an appropriate alignment relative to the other adjacent vertebral bodies. As explained above, other optional steps within the skill of an ordinary artisan, such as a surgeon familiar with spinal surgeries discussed herein, may be employed. For example, a construct as explained herein with an upper and lower nut may provide a surgeon the ability to "dial in" the construct to raise and/or lower vertebral bodies while also keeping and/or adjusting a longitudinally extending rod at an appropriate elevation. For example still, a surgeon may raise the rod, lower the rod, raise the rod again, lower the rod again, etc. in any number of discrete steps to achieve the desired goals of the surgeon as may be dictated by the patient specific anatomy and procedure.

It should be understood that various aspects disclosed herein may be combined in different combinations than the combinations specifically presented in the description and accompanying drawings. For example, features, functionality, and components from one embodiment may be combined with another embodiment and vice versa unless the context clearly indicates otherwise. Similarly, features, functionality, and components may be omitted unless the context clearly indicates otherwise. It should also be understood that, depending on the example, certain acts or events of any of the processes or methods described herein may be performed in a different sequence, may be added, merged, or left out altogether (e.g., all described acts or events may not be necessary to carry out the techniques).

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

What is claimed is:

1. An implant, comprising:
   an implant receiver having a base and a first arm and a second arm extending from the base in a longitudinal direction, the first arm and second arm defining a receiving cavity extending between the first arm and second arm in the longitudinal direction from the base to an open end opposite the base,
   the first arm having a first outside thread pattern extending in the longitudinal direction on an outside surface of the first arm and a first inside thread pattern extending in the longitudinal direction on an inside surface of the first arm;
   the second arm having a second outside thread pattern extending in the longitudinal direction on an outside surface of the second arm and a second inside thread pattern extending in the longitudinal direction on an inside surface of the second arm;
   a set screw having a third outside thread pattern extending along an outside circumferential surface of the set screw, the third outside thread pattern having a size and shape corresponding to a size and shape of the first inside thread pattern and a size and shape of the second inside thread pattern; and
   a nut having a third inside thread pattern extending along an inside circumferential surface of the nut, the third inside thread pattern having a size and shape corresponding to a size and shape of the first outside thread pattern and a size and shape of the second outside thread pattern,
   wherein the nut is positionable beneath a rod extending through the receiving cavity such that a top surface of the nut supports the rod.

2. The implant of claim 1, further comprising the rod.

3. The implant of claim 1, wherein the base includes a coupling cavity configured to couple to a bone screw.

4. The implant of claim 3, wherein the bone screw is a multi-axial bone screw.

5. The implant of claim 1, comprising:
a crown having a fourth outside thread pattern extending on an outside circumferential surface of the crown;
wherein:
a lower portion of the inside surface of the first arm proximate the base comprises a fourth interior thread pattern,
a lower portion of the inside surface of the second arm proximate the base comprises a fifth interior thread pattern, and
the fourth outside thread pattern has a size and shape corresponding to a size and shape of the fourth interior thread pattern and a size and shape of the fifth interior thread pattern.

6. The implant of claim 5, wherein the crown comprises a drive end and an open end opposite the drive end, the open end being configured to fix a relative angular orientation of the implant with respect to a multiaxial bone screw.

7. The implant of claim 1, comprising:
the rod; and
a bone screw,
wherein:
the receiving cavity is configured to receive the rod through the open end such that the rod extends through the receiving cavity in a direction that is substantially perpendicular to the longitudinal direction, and
the base of the implant receiver comprises a coupling cavity configured to couple to the bone screw.

8. The implant of claim 7, wherein the nut is rotatable around the first outside thread pattern and second outside thread pattern such that the nut is movable in the longitudinal direction between a plurality of elevations between the base and the open end.

9. The implant of claim 1, wherein the nut circumscribes the first arm and second arm.

10. The implant of claim 1, wherein the nut is movable in the longitudinal direction from the base to the open end between a plurality of different elevations.

11. The implant of claim 10, further comprising:
a top nut having a fourth inside thread pattern extending along an inside circumferential surface of the top nut, the fourth inside thread pattern having a size and shape corresponding to a size and shape of the first outside thread pattern and a size and shape of the second outside thread pattern,
wherein the top nut is positionable above the rod extending through the receiving cavity such that a bottom surface of the nut contacts the rod.

12. The implant of 11, wherein the set screw is configured to press against the rod while it is supported by the nut at any one of the plurality of different elevations.

13. The implant of claim 1, wherein the set screw is a break off set screw.

14. The implant of claim 1, wherein:
a minor diameter of the first outside thread pattern is at an elevation corresponding to an elevation of a major diameter of the first inside thread pattern, and
a minor diameter of the second outside thread pattern is at an elevation corresponding to an elevation of a major diameter of the second inside thread pattern.

15. The implant of claim 1, wherein the first arm comprises a first plurality of breakoff locations and the second arm comprises a second plurality of breakoff locations.

16. A method for installing a spinal implant, comprising:
providing
an implant receiver having a base and a first arm and a second arm extending in a longitudinal direction from the base to an open end, the first arm and second arm defining a receiving cavity extending between the first arm and second arm in the longitudinal direction from the base to the open end;
providing a nut having an upper surface and a lower surface opposite the upper surface;
securing the implant receiver to a bone screw;
reducing a rod to an intermediate elevation by pushing the rod through the open end into the receiving cavity, the intermediate elevation being between the base and the open end; and
supporting the rod at the intermediate elevation by the nut such that the upper surface of the nut faces the rod and the lower surface of the nut faces the bone screw.

17. The method of claim 16, wherein:
the first arm has a first outside thread pattern extending in the longitudinal direction on an outside surface of the first arm;
the second arm has a second outside thread pattern extending in the longitudinal direction on an outside surface of the second arm;
the nut has a third inside thread pattern extending along an inside circumferential surface of the nut; and
further comprising
moving the nut to the intermediate elevation by rotating the nut around the first outside thread pattern and second outside thread pattern such that the nut is linearly translated in the longitudinal direction to the intermediate elevation.

18. The method of claim 17, further comprising tightening a set screw against the rod thereby pushing the rod against the upper surface of the nut.

19. The method of claim 18, further comprising breaking off a portion of the set screw.

20. The method of claim 19, comprising:
breaking off an upper portion of the first arm; and
breaking off an upper portion of the second arm.

21. A method for installing a spinal implant, comprising:
providing:
an implant receiver having a base and a first arm and a second arm extending in a longitudinal direction from the base to an open end, the first arm and second arm defining a receiving cavity extending between the first arm and second arm in the longitudinal direction from the base to the open end, wherein the first arm has a first outside thread pattern extending in the longitudinal direction on an outside surface of the first arm and the second arm has a second outside thread pattern extending in the longitudinal direction on an outside surface of the second arm;
securing the implant receiver to a bone screw;
reducing a rod to an intermediate elevation by pushing the rod through the open end into the receiving cavity, the intermediate elevation being between the base and the open end;
supporting the rod at the intermediate elevation;
providing a nut having a third inside thread pattern extending along an inside circumferential surface of the nut;
moving the nut to the intermediate elevation by rotating the nut around the first outside thread pattern and second outside thread pattern such that the nut is linearly translated in the longitudinal direction to the intermediate elevation;

supporting the rod at the intermediate elevation further comprises supporting the rod by an upper surface of the nut; and tightening a set screw against the rod thereby pushing the rod against the upper surface of the nut.

* * * * *